United States Patent [19]

Klepacki

[11] Patent Number: 4,687,441
[45] Date of Patent: Aug. 18, 1987

[54] ELASTOMERIC SECURING MEANS FOR ORTHODONTIC APPLIANCES

[76] Inventor: Frank H. Klepacki, 6240 S. County Line Rd., Burr Ridge, Ill. 60521

[21] Appl. No.: 732,567

[22] Filed: May 10, 1985

[51] Int. Cl.⁴ .............................................. A61C 7/00
[52] U.S. Cl. ...................................................... 433/8
[58] Field of Search .......................... 433/8, 9, 11, 13; 215/321; 150/52 L, 52 R

[56] References Cited

U.S. PATENT DOCUMENTS

| | | | |
|---|---|---|---|
| 1,304,193 | 5/1919 | Nicholls | 215/321 |
| 1,435,214 | 11/1922 | Coombs | 215/321 |
| 2,699,809 | 1/1955 | Nebe et al. | 150/52 L |
| 2,767,469 | 10/1956 | Gladstone | |
| 3,530,583 | 9/1970 | Klein et al. | |
| 4,107,844 | 8/1978 | Kurz | 433/4 |
| 4,180,912 | 1/1980 | Kesling | 433/8 |

Primary Examiner—Robert Peshock
Attorney, Agent, or Firm—Keil & Weinkauf

[57] ABSTRACT

An elastomeric device for use with an orthodontic appliance of the type wherein an archwire is inserted in the archwire slot formed in a bracket, attachable to a patient's tooth, which has hook-shaped projections formed therein. The elastomeric device includes a unit having a closed loop portion which is stretchable over the projections for holding the archwire to the bottom of the slot, and a cap portion integrally molded with the loop portion for covering the bracket. The cap portion protects the oral cavity of the patient against irritation from the rough surfaces of the bracket, keeps food particles from becoming lodged in the crevices of the bracket, and enhances the appearance of the overall appliance by hiding the bracket from view. The elastomeric device may be in the form of a single unit or in the form of an integrally molded chain-like arrangement of such units.

7 Claims, 7 Drawing Figures

ELASTOMERIC SECURING MEANS FOR ORTHODONTIC APPLIANCES

BACKGROUND OF THE INVENTION AND PRIOR ART

The invention relates to a flexible device for use with an orthodontic appliance comprising a bracket which is attached to a patient's tooth and has projections, and has an archwire slot formed therein.

In the art of orthodontics, the use of various forms of tension-applying devices are known for properly locating an archwire in a bracket or brackets, and also for repositioning teeth towards or away from each other.

For example, U.S. Pat. No. 2,767,469, which issued to Gladstone on Oct. 29, 1963, has an archwire lock in the form of an endless loop of resilient material which is harmless to human tissue and resistant to mouth secretions. This lock of flexible material is used in the Gladstone reference in connection with an orthodontic bracket of the wing type, that is with a bracket having hook-shaped projections in which an archwire slot is formed. In use the flexible loop is placed over the wings of the bracket and in this manner the archwire is urged into, and held in place in, the slot.

Today flexible loops of this kind made of elastomeric material are on the market. As shown, for example, in U.S. Pat. No. 3,530,583 issued to Klein et al on Sept. 27, 1970, such elastomeric loops or o-rings can be made as individual modules or as a chain of a plurality of such modules, in which latter case the flexible links between the modules when placed on the brackets serve to apply a tension between adjacent brackets and hence to the teeth to which the brackets are attached, to pull these teeth toward one another.

OBJECTS AND SUMMARY OF THE INVENTION

The principal object of the invention is the provision of a novel design of such elastomeric devices which, while retaining the above tension-applying function—to secure the archwire and, if desired, to pull adjacent teeth together—greatly enhances their utility by simultaneously using them as a means for covering the brackets with their sharp and unsightly projections.

A more particular object of the invention is to design the elastomeric devices in question in such a way that they not only perform the aforementioned tension-applying function but also substantially reduce irritation of the patient's lips and cheeks by the projections of the bracket; substantially reduce the entrapment of food particles in the bracket; and, in addition, substantially improve the appearance of the appliance assembly and thus help to minimize potential embarrassment to the wearer of the orthodontic appliance.

With the foregoing objects in mind the invention in its principal aspect consists, briefly, in an elastomeric device for use with an orthodontic appliance comprising at least one bracket which is attachable to a patient's tooth and has hook-shaped projections and an archwire slot formed therein, the elastomeric device including at least one unit having a closed loop portion stretchable over the projections for holding the archwire down in the slot, and a cap portion integrally molded with the loop portion for covering the bracket.

Preferably the cap portion for greater flexibility has a thickness less than that of the loop portion. Also, preferably the maximum circumferential dimension of the cap portion is larger than that of the loop portion. This makes it possible for the cap portion to readily extend over the wings of the bracket and to substantially "hug" the face of the latter.

BRIEF DESCRIPTION OF THE DRAWINGS

Preferred embodiments of the invention will now be described in greater detail with reference to the accompanying drawings in which.

DETAILED DESCRIPTION OF THE PREFERRED EMBODIMENTS

Figure 1:
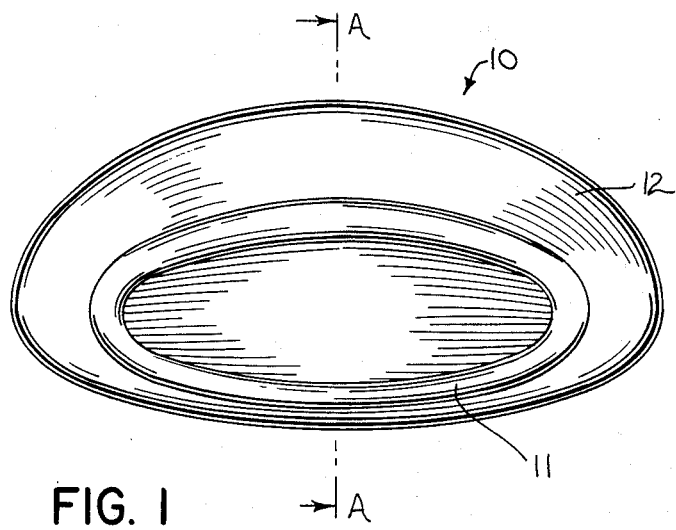
FIG. 1 is a perspective view, from below, of a first embodiment in the form of an individual elastomeric unit according to the invention.
Figure 2:
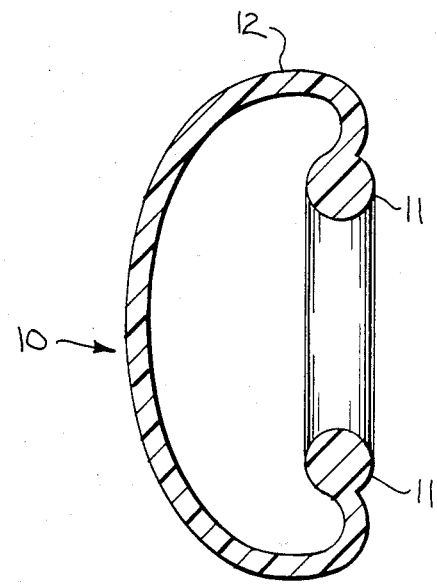
FIG. 2 is a cross-section, taken along line A—A of FIG. 1 of the individual elastomeric unit according to the invention.

Referring first to FIGS. 1 and 2, there is shown a first embodiment of the invention in which the elastomeric device 10 is in the form of an individual unit having a tension-applying closed-loop portion 11 and a cap portion 12. The device is molded of a suitable elastomeric material which is tough and also is resistant to mouth fluid, in short, of a material which is capable to withstand large periods of use under conditions generally associated with the oral cavity. A material that has been found especially satisfactory for this application is an elastomeric, thermoset-thermoplastic, polyester-based isocyanide terminated, urethane resin. Material of this type is commercially available.

The unit is preferably of circular shape as manufactured—although after its application to a bracket by stretching, it may assume a slightly different, for example, an oblong shape. However, while the unit has been shown in the drawings as of circular form, it can also be produced in a variety of other shapes such as essentially rectangular or square with rounded corners. Depending on its use, the unit could be made in graduated sizes. A suitable manufacturing process for the elastomeric unit according to the invention is by injection molding using split molds.

As will be seen from FIGS. 1 and 2, the cap or dome portion 12, for greater flexibility, has a thickness less than that of the loop portion 11, typically the thickness of the cap portion should be only about half of that of the loop portion. In a preferred embodiment the thickness of the cap portion was in the range of 0.007–0.015" while that of the loop portion was in the range of from 0.030–0.050". This reduced thickness of the cap portion makes it possible for this portion to substantially "hug" the surfaces of the bracket as the unit is placed on the wings of the bracket. It will also be seen from FIGS. 1 and 2 that the maximum circumferential dimension of the cap portion is greater than the peripheral diameter of the ring portion, to enable the unit to be slipped over the wings of the bracket without difficulty.

Figure 3:
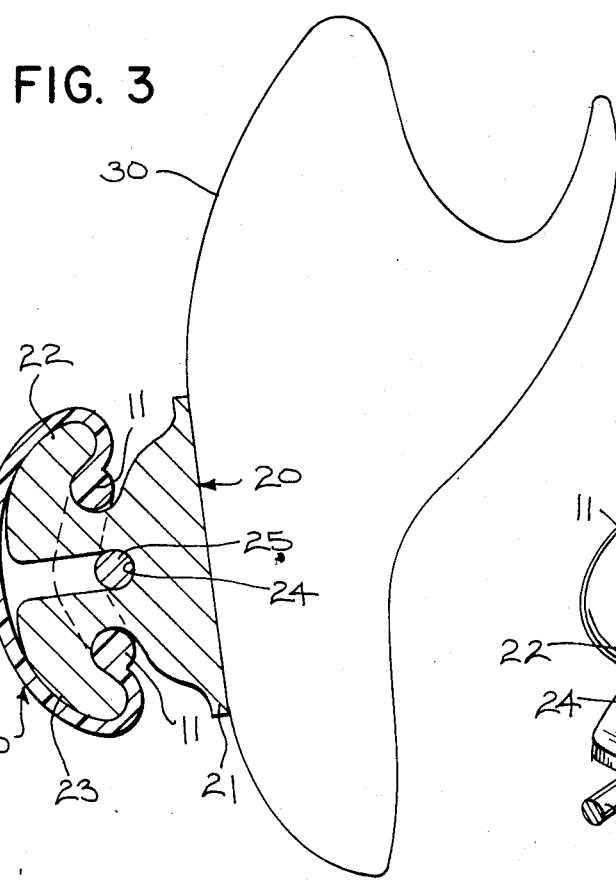
FIG. 3 is a cross-section similar to that of FIG. 2 but showing the elastomeric unit applied to a bracket, with the bracket attached to a tooth and an archwire inserted in the archwire slot of the bracket.
Figure 4:
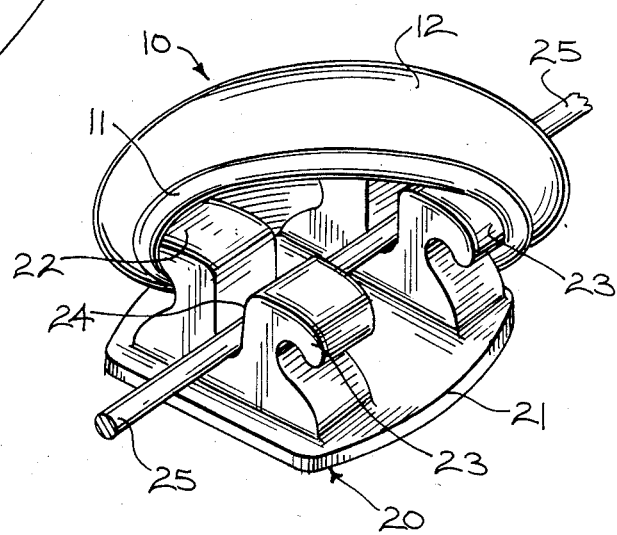
FIG. 4 is a perspective view showing an archwire inserted in the archwire slot of a bracket and the elastomeric unit in process of being placed over the bracket and the archwire.

The foregoing design features will become clearer from an inspection of FIG. 3 in which the elastomeric unit according to FIGS. 1 and 2 has been illustrated applied to a bracket 20 which has been attached to a tooth 30 by bonding base 24 of the bracket to the labial face of the tooth. As shown in FIG. 3, and also in FIG. 4, which illustrates the elastomeric unit 10 in the process of being applied to the bracket 20, the bracket has two pairs of opposing, hook-shaped projections or wings 22,23, with an archwire slot 24 formed in aligned relationship, between the wings of each pair. The archwire, designated 25 is shown inserted in this slot. In order to secure the archwire in place in slot 24, elastomeric unit 10 is placed over the wings and over the archwire in the manner shown in FIG. 4 and is then pulled, by stretching, over the remaining wing or wings with a suitable tool until the ring portion 11 of the unit snaps into the recesses underneath the wings. A so-called mosquito needle holder in which the open part of the elastomeric unit is impaled as it were, has been found to be a useful tool for pulling the unit according to the invention over the bracket. In the seated position the ring portion 11 contacts archwire 25 at two opposite points from above and thereby urges the archwire against the bottom of slot 24.

In the process, cap portion 12 of unit 10 has been draped over the top surfaces of the wings and it thereby forms a smooth, semisoft, resilient cover for the bracket. This cover protects the mouth cavity from irritation or injury by the rough contours of the wings, keeps food particles from becoming lodged in the crevices of the bracket, and hides the bracket from view when the patient opens his mouth. The great majority of orthodontic brackets of this general kind are made of metal, and particularly in connection with such brackets, it is advantageous to make the orthodontic unit of the invention of a color having a shade simulating the tooth color. In this case the unsightly metallic appearance of such brackets is thus eliminated. If additional color matching is desired, the elastomeric unit could be provided in a variety of colors or shades.

Figure 5:
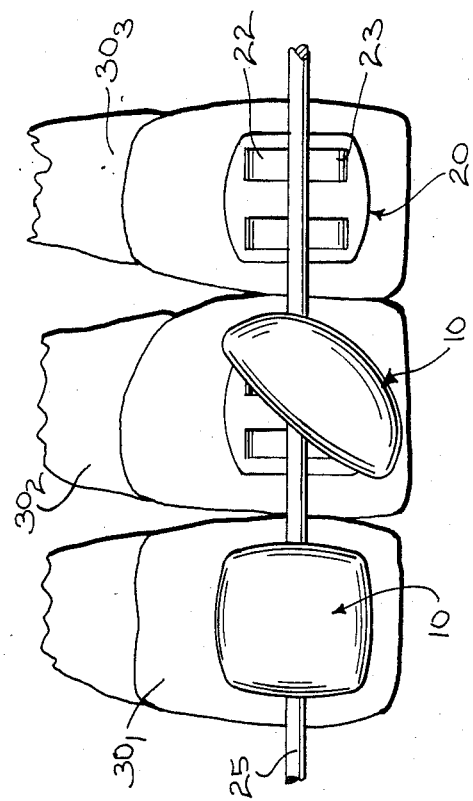
FIG. 5. is a front view of three adjacent teeth having respective brackets attached thereto, the bracket shown on the left having an individual unit according to the invention placed thereon and thus being hidden from view, and a second elastomeric unit being in the process of being placed on the bracket attached to the tooth in the center.

In FIG. 5 three adjacent teeth $30_1$, $30_2$ and $30_3$ are shown, each having a bracket 20 mounted thereon by bonding, and an archwire 25 being inserted into the archwire slots of the brackets. The bracket attached to the tooth on the right is fully visible. The bracket mounted on the center tooth is partially obscured since an individual elastomeric unit 10 of the kind shown in FIGS. 1–4 is assumed in process of being placed on this bracket. In the case of the tooth on the left the elastomeric unit 10 according to the invention is shown fully applied to the corresponding bracket. This particular bracket therefore is invisible since it is completely covered by the cap portion of this elastomeric unit.

Figure 7:
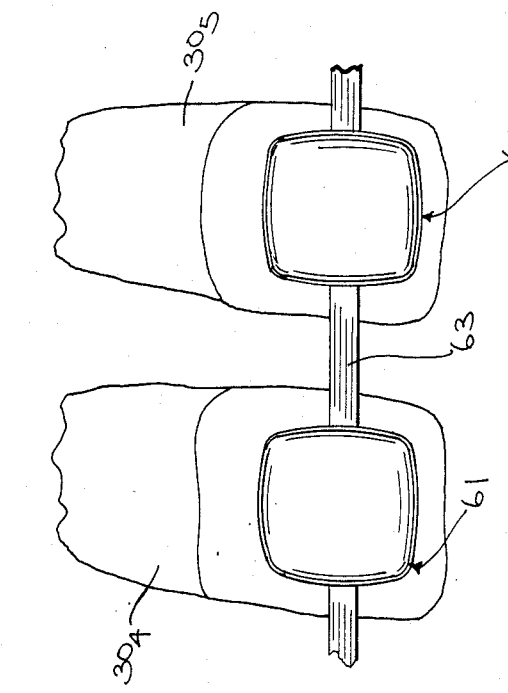
FIG. 7 is a front view of two excessively spaced teeth and two units of an integrally molded chain of such units applied to the brackets, not visible in the figure, of the respective teeth, the integrally molded linking section between the two units applying the tension for pulling the two teeth closer to each other.
Figure 6:
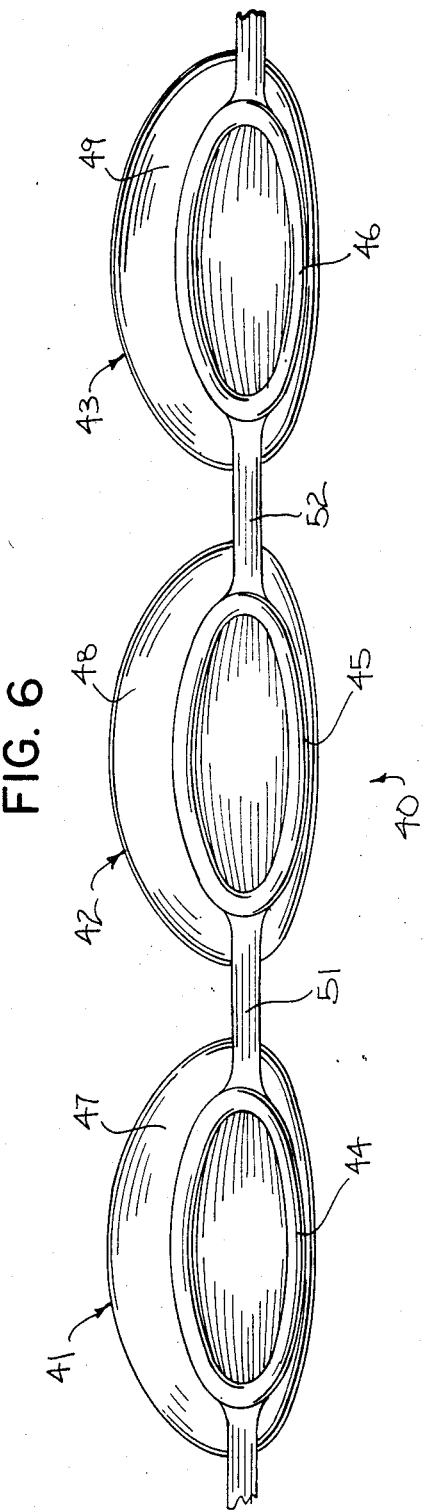
FIG. 6 is a perspective view of a second embodiment of the invention in which the elastomeric device consists of an integrally molded chain of a plurality of individual elastomeric units according to the invention, with the ring portions of adjacent units interconnected by integrally molded, tension-applying linking sections which tend to move the brackets and hence the teeth towards each other.

FIGS. 6 and 7 illustrate the second embodiment of the present invention. Thus, FIG. 6 shows a chainlike formation of three elastomeric units 41,42 and 43 having closed loop portions 44,45,46 and cap portions 47,48,49, respectively. As will be seen from FIG. 6, the loop portions of adjacent two of the individual units are interconnected by link sections 51 and 52. The entire series arrangement or chain including the loop portions, the cap portions and the linking sections is integrally molded of elastomeric material of the above-mentioned—general or specific—kind.

The chain may comprise more than the three units shown in FIG. 6 and the particular chain length desired for any given orthodontic application may be obtained by snipping the desired length off from the overall chain, in fact this overall chain itself may be provided, as a stock item in the form of an endless loop. It is also possible to mold the chain integrally with a carrier element (not shown) of corresponding length, the chain being connected with the carrier element by short bridge portions at predetermined points, for example at the closed loop portions, in which case the chain wanted for a given task could be severed from the carrier element at these points to establish the desired length. Techniques of this general kind are known in the art.

FIG. 7 illustrates how the linking sections can be used to produce a tractive force for pulling two adjacent, excessively spaced teeth together. The figure shows two such teeth $30_4$ and $30_5$ each having a bracket attached thereto, with each individual unit 61,62 according to the invention applied over the bracket in such a way that the linking section 63 is in stretched condition after units 61,62 have been placed in position on their respective brackets. Since the cap portions of these units cover the corresponding brackets, the brackets themselves are hidden from view in FIG. 7.

The link sections such as 63 in FIG. 7, which, as mentioned form a part of the integrally molded chain, are designed and dimensioned to exert a sufficient tractive force on the teeth, $30_4$, $30_5$, to pull these teeth together over the period of the orthodontic treatment. Preferably these linking sections are also designed and dimensioned to conceal the lengths of archwire underneath them from view. Such a design and such dimensions have been assumed in FIG. 7 in which the archwire, in its turn, is hidden from view. With the foregoing in mind, the linking sections could be made in a variety of cross-sectional shapes, such as round, oval, flat or crescent shaped; and the thickness and the length of these sections could be chosen to meet the requirements of the specific task at hand.

More generally it should be emphasized that the embodiments described and illustrated are given herein by way of example only and the invention should not be construed as being limited thereby. Also the brackets in connection with which the elastomeric units are used may have a design different from that shown herein.

What is claimed is:

1. In combination with an orthodontic appliance comprising at least one bracket which is attachable to a patient's tooth, has an archwire slot formed therein endwise of said bracket and has hook-shaped projections defining recesses therebelow on either side of said slot, an elastomeric device including at least one unit having a closed loop portion stretchable over said projections and seated in said recesses, said recesses being at a level sufficiently low that said loop portion, upon being seated, urges said archwire downwardly at points adjacent the two opposite ends of the bracket to hold the archwire down in said slot and a cap portion integrally molded with said loop portion for covering said bracket, said cap portion having a maximum circumferential dimension larger than that of said loop portion to facilitate accommodation of said projections in said cap portion.

2. An elatomeric device as claimed in claim 1, wherein the cap portion for greater flexibility has a thickness less than that of the loop portion.

3. An elastomeric device as claimed in claim 2, wherein the cap portion has a thickness of 0.007" to 0.015" whereas the loop portion has a cross-sectional diameter of 0.30" to 0.050".

4. An elastomeric device as claimed in claim 1, wherein said unit is of substantially circular shape.

5. An elastomeric device as claimed in claim 1, wherein said device includes a plurality of said units, each having a closed loop portion and a cap portion, and, integrally molded with said units, tensioning link means interconnecting the loop portions of adjacent ones of said units.

6. An elastomeric device as claimed in claim 5, wherein said link means are dimensioned and/or shaped to cover the archwire.

7. An elastomeric device as claimed in claim 1, wherein said device is of tooth colored material.

* * * * *

UNITED STATES PATENT AND TRADEMARK OFFICE
CERTIFICATE OF CORRECTION

PATENT NO. : 4,687,441
DATED : Aug. 18, 1987
INVENTOR(S) : KLEPACKI

It is certified that error appears in the above-identified patent and that said Letters Patent are hereby corrected as shown below:

Title page:

[76] Line 1   before "6240" insert -- 1501 Burr Ridge Club Drive --

Col. 6 Line 4 "0.30" should be -- .030 --

Signed and Sealed this

Twelfth Day of January, 1988

Attest:

DONALD J. QUIGG

Attesting Officer      Commissioner of Patents and Trademarks